United States Patent [19]
Faenger et al.

[11] Patent Number: 5,584,826
[45] Date of Patent: Dec. 17, 1996

[54] DEVICE AND METHOD FOR ASSISTING IN THE REMOVAL OF FLUID FROM A HUMAN BEING

[75] Inventors: Barbara Faenger, St. Louis, Mo.; S. Glenn Scott, Memphis, Tenn.; James Uttendorf, St. Charles, Mo.

[73] Assignee: Professional Specialties Co., St. Louis, Mo.

[21] Appl. No.: 389,334

[22] Filed: Feb. 14, 1995

[51] Int. Cl.[6] .................................................. A61M 1/00
[52] U.S. Cl. ..................... 604/322; 604/317; 128/760; 128/768; 297/188.08; 5/503.1; 280/304.1
[58] Field of Search .................... 604/317–322, 604/326, 331; 128/760, 768, 877, DIG. 26; 280/304.1, 304.5; 5/604, 606, 503.1; 297/188.01, 188.08, 188.02, 188.12; 150/150

[56] References Cited

U.S. PATENT DOCUMENTS

| | | | |
|---|---|---|---|
| 1,658,294 | 2/1928 | Lewis | 150/150 |
| 3,259,920 | 7/1966 | Voller | 604/326 |
| 3,896,809 | 7/1975 | Samuel et al. | 604/326 |
| 4,179,159 | 12/1979 | Sieklucki et al. | 604/322 |
| 4,861,059 | 8/1989 | Shirk | 280/304.1 |
| 4,888,005 | 12/1989 | Dingeman et al. | 604/326 |
| 4,997,426 | 3/1991 | Dingeman et al. | 604/322 |
| 5,015,033 | 5/1991 | Winters | 297/188.12 |
| 5,106,152 | 4/1992 | Ward, Sr. et al. | 297/188.12 |
| 5,180,181 | 1/1993 | Letechipia | 280/304.1 |

*Primary Examiner*—John G. Weiss
*Assistant Examiner*—Dennis Ruhl
*Attorney, Agent, or Firm*—Foley & Lardner

[57] ABSTRACT

A device for assisting in the removal of fluid from a human being. A member is provided for supporting the human being above a ground plane. An end of a tube is connected to a catheter which in turn is inserted in or attached to the human being. The other end of the tube is connected to a fluid retrieval container. The fluid retrieval container is attached to the member. A holder is disposed on the member to retain and release an excess length of tube extending between the human being and the fluid retrieval container. The holder retains the excess tube in an operative position which assists in the gravitational effects of fluid flowing through the tube.

2 Claims, 2 Drawing Sheets

5,584,826

DEVICE AND METHOD FOR ASSISTING IN THE REMOVAL OF FLUID FROM A HUMAN BEING

BACKGROUND OF THE INVENTION

1. Field of the Invention

This invention relates to a device and method for assisting in the drainage of fluid from a human being. More particularly, the invention relates to a device for assisting in the gravitational effects on fluid flowing through a catheter into tubing and a collection device.

2. Related Art

Typically, a catheter is inserted in or attached to a human being when the human being is located in a bed or on a stretcher. A tube is usually provided between the catheter and a fluid retrieval container or drain bag. Due to the distance from the attachment point of the tube to the catheter and the fluid retrieval container or drain bag, the tube generally is set at a standard length. When the human being or patient is transported or moves from the bed to a chair or wheelchair, an excessive amount of tube remains between the catheter and the fluid retrieval bag.

Rather than replacing the existing catheter tube with a shorter tube each time the patient moves from the bed to a chair or wheelchair, in some instances, the catheter tube is simply left to dangle freely or is bunched or coiled up beside the patient. In such instances, a portion of the catheter tube may fall below the level of the fluid in the retrieval container or drain bag. When this happens, the fluid can back up in the tube and the back up can lead to urinary track infections.

Moreover, by allowing the excess tube to dangle around the patient in an unprotected manner, the tube maybe susceptible to damage. Additionally, if the excess portion of the tube is stepped on or accidentally caught within or beneath a wheel of the wheelchair, the tube may be forcibly pulled away from the patient, thereby possibly causing the patient discomfort and/or injury, and disrupt the sterile closed system, thus increasing the chance for urinary tract infection.

SUMMARY OF THE INVENTION

One of the objectives of the invention is to provide a device that assists in the removal of fluid from a human being. The device assists in the removal of fluid from a human being by placing the excess tube between the catheter inserted in or attached to the patient and a fluid retrieval container in an operative position which assists in the gravitational effects on the fluid flowing through the tube.

This objective is achieved by providing a tube having a first end, a middle portion, and a second end. The first end of the tube is operatively attached to the catheter which in turn is inserted in or attached to the human being or patient. The second end of the tube is connected to a fluid retrieval container or drain bag. The human being and the fluid retrieval container are supported by a support member. A holder is disposed on the support member between the connection points of the first and second ends of the tube to the catheter and the fluid retrieval container, respectively, in order to aid in the flow of the fluid through the tube. The holder retains the excess or middle portion of the tube in an operative location.

Another objective of the invention is to provide a holder which functionally retains an excess middle portion of the tube when a patient is located on a support member such that there is no excess tube lying between the patient and the fluid retrieval container. This objective is achieved by providing a holder configured such that it retains the excess tube and releases the excess tube when a predetermined force is applied on the tube. The predetermined force is usually applied by the patient rising up from the support member or being moved along the support member.

This objective is further accomplished by providing the holder as an integral part of the support member and/or with a material that has a rigidity strong enough to retain the excess tube but has enough flexibility to allow the tube to come out of the holder when the tube is pulled by the predetermined force.

Another objective of the invention is to provide a protective system for the excess tube extending between the catheter inserted in or attached to patient and the fluid retrieval container.

This objective of the invention is achieved by providing a holder in the form of a pouch. The pouch comprises a first portion of material connected to a second portion of material. The two portions of material are joined together along each of their corresponding sides except one pair of sides which remain unconnected to form a pouch opening. The pouch is used in conjunction with the support member to provide a protective arrangement for the excess tubing.

A further objective of the invention is to provide a method of assisting in the flow of fluid from a human being. This method is accomplished by providing a member which supports the human being above a ground plane. The method further involves holding a fluid retrieval container on the member which supports the human being; attaching a first end of the tube to a catheter which in turn is inserted in or attached to the human being; attaching a second end of a tube to the fluid retrieval container; and disposing a pouch or holder on the member.

The device and method according to the invention that provides the objectives as stated above will become apparent from the detailed description given hereafter. It should be understood, however, that the detailed description, while indicating a preferred embodiment of the invention, is given by way of illustration only since various changes and modifications within the spirit and scope of the invention will become apparent to those skilled in the art.

DETAILED DESCRIPTION OF THE PREFERRED EMBODIMENTS

Figure 1:
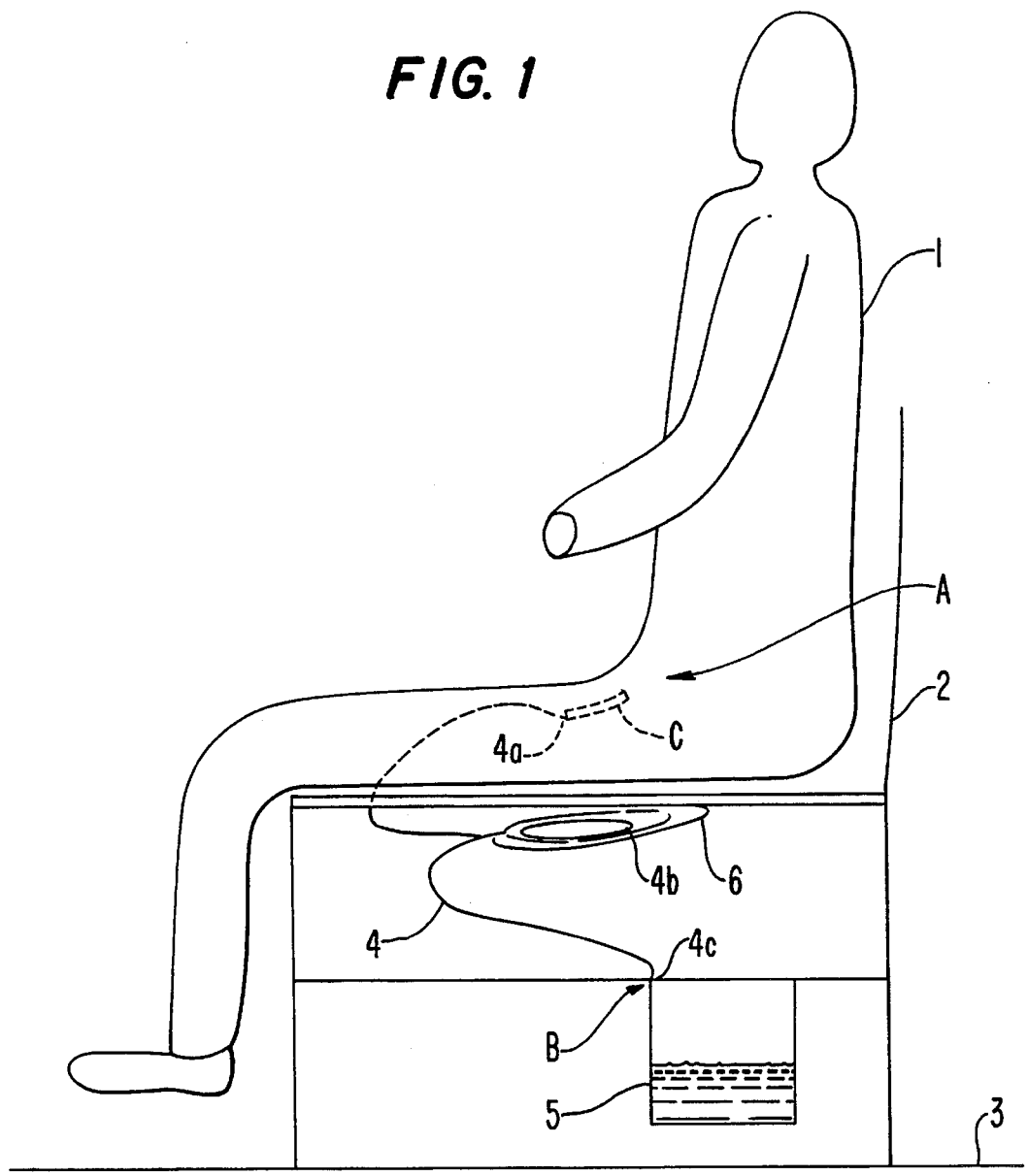
FIG. 1 shows a side view of a first embodiment of the device of the present invention.

FIG. 1 shows the first embodiment of the present invention. A schematic representation of a human torso 1 is shown on a support member 2. As shown in FIG. 1, the support member is a chair. Alternatively, the support member may be either a bed, a wheelchair, a geriatric chair (geri chair), a stretcher or any other structural arrangement which can support a human being above the ground plane 3.

A first end 4a of a tube 4 is attached to a catheter C. The catheter C is connected to the torso 1 by inserting the catheter in or attaching the catheter to the torso 1 at a first position A. A second end 4c of the tube 4 is connected at a second position B to a fluid retrieval container or drain bag 5.

A middle portion of the tube 4b is retained in a holder 6. The holder 6 is attached to the support member 2 by a fastener. The fastener can take the form of a hook and loop fastener, glue, tape, staples, screws, nails, or any other suitable fastening device.

The holder 6 is arranged on the support member 2 such that it aids in the gravity flow of fluid through the tube 4. Although FIG. 1 shows the holder 6 disposed in a direct horizontal arrangement with respect to the ground plane 3, the holder 6 may be held in a vertical or oblique relationship to the ground plane.

The holder 6 retains the middle portion 4b of tube 4 at an operative position above the ground plane 3. The operative position corresponds to the location where placement of the middle portion 4b of tube 4 enhances the gravitational effects on the fluid flowing through the tube 4. The operative position is preferably located between the first position A and second position B, with respect to the ground plane 3.

Although shown in FIG. 1 as a separate device, the holder 6 may be made of material that is integrally formed with the support member 2. For example, the holder 6 may be a pocket formed from a single piece of material with the material which is used to form the seat of a chair or wheelchair. Furthermore, the holder 6 may take the form of a clip, or any retaining device. The holder can comprise metal, plastic, or any other suitable material.

Whichever form the holder 6 takes, the holder must retain the excess middle portion 4b of the tube when the patient is in the sitting position shown in FIG. 1. Furthermore, the holder must be arranged to operatively release the middle portion of the tube 4b when pulled such that the holder releases the tube without forcibly removing the end of the tube 4a from the catheter C, and/or the catheter C from the patient.

Figure 2:
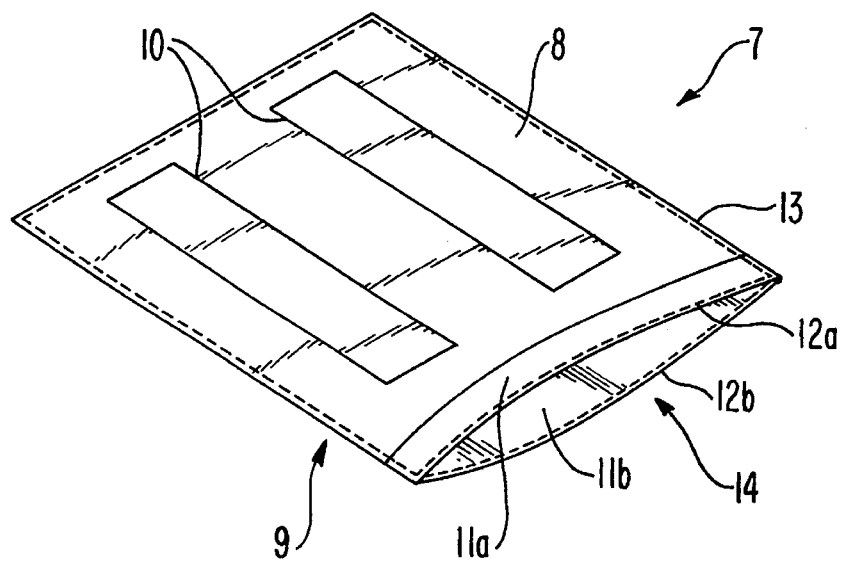
FIG. 2 shows a perspective view of a first embodiment of the holder of the present invention.

Although the holder 6 may take the form of a clip or pocket retainer as shown in FIG. 1, an alternative preferred embodiment of the holder 6 is in the form of a rectangular pouch 7 shown in FIG. 2.

The pouch 7 is provided with a first material portion 8 and a second material portion 9, which is disposed opposite to the first material portion. As shown in FIG. 2, the first material portion 8 is joined to the second material portion 9 along three of their corresponding sides. The sides are connected by any suitable arrangement. In a preferred embodiment, the sides are connected by folding a portion of the first and second material portions, and then stitching the corresponding sides together. The remaining unjoined corresponding sides of the first and second material portion form a pouch opening 14.

In a preferred embodiment, the first material portion 8 and second material portion 9 are formed from a single rectangular sheet of material folded in half along a central axis. The fold in the single sheet of material creates the corresponding sides of the first and second material portions. The remaining sides of the first and second material portions 8, 9 can be joined by any suitable connecting arrangement, such as stitching, glue, tape or staples. A threaded stitching 13, however, is used in the preferred embodiment shown in FIG. 2.

Figure 3A:
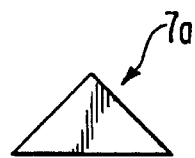
FIGS. 3A–3C show alternative embodiments of the holder shown in FIG. 2.
Figure 3B:
Figure 3C:
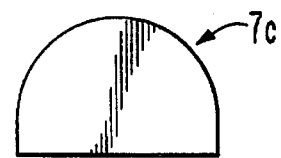

FIGS. 3A–3C show alternative shapes (triangle 7a, square 7b, semi-circle 7c) which the pouch 7 may have. Although three different arrangements have been shown, it is to be understood that the pouch 7 can be any shape as long as it has an opening for receiving a portion of the tube 4.

Each of the three embodiments shown in FIGS. 3A–3C can be formed from a single sheet of material. Alternatively, the various pouches illustrated can be made from two or more pieces of material joined together.

Connected to an exterior side of the first material portion 8 or second material portion 9 is a fastener 10 which fastens the pouch 7 to the support member 2.

The fastener 10, as discussed above, may encompass various forms of standard fastening devices. Preferably, as shown in FIG. 2, a hook and loop fastener is used with the preferred embodiment of the holder 6.

In another preferred embodiment, the pouch opening 14 is provided with a stiffener 11a, 11b. The stiffener 11a, 11b assists the pouch 7 in performing its function of holding the middle portion 4b of the tube, and releasing the tube 4 when a pulling force is applied to the tube. In the pouch 7 shown in FIG. 2, the first material portion 8 of the pouch is provided with a stiffener 11a. The stiffener 11a is held within a pocket 12a formed in the first material portion. A second stiffener 11b is provided in the second material portion 9. The stiffener 11b is provided in a pocket 12b formed in the second material portion 9. The stiffeners 11a and 11b may be made of plastic, metal, or any other material which will allow the stiffeners 11a, 11b to perform the required holding and releasing function.

Each of the pockets 12a, 12b is formed by a folded section of the respective first and second material portions 8, 9. Each pocket 12a, 12b can be secured in a closed position by any suitable material connection device, as shown in FIG. 2, stitching is used.

The stiffeners 11a and 11b are provided in the pouch opening 14 for operatively holding the middle portion 4b of the tube 4 in the pouch 7 when the patient is in a position such as shown in FIG. 1. The stiffeners 11a and 11b in the pouch opening 14 allow the middle portion 4b of the tubing 4 to be removed from the pouch 7 without hesitation or resistance when the tube is pulled with a predetermined force. The predetermined force is less than the force required to forcibly remove the tube from the catheter, and/or the catheter from the human being.

Although pouch 7 is shown with stiffeners 11a and 11b in order to assist in the retention of the middle portion of the tube, the pouch may be provided without these stiffeners. If the pouch is provided without stiffeners, the material that is used to make the pouch must have a flexibility that allows the pouch to carry out the retaining and releasing function of the tube.

The pouch 7 may be made of numerous materials. In a preferred embodiment, the pouch is made of vinyl.

It will be understood that various modifications in the form of the invention as described herein in its preferred embodiments may be made without departing from the spirit thereof and the scope of the claims which follow.

What is claimed is:

1. A device for assisting in the removal of fluid from a human being, said device comprising:

a fluid retrieval container;

a tube having a first end, a middle portion, and a second end, said first end being attached to a catheter, said catheter being connectable to a human being, said second end being connected to said fluid retrieval container;

a support member, said support member supporting said human being and said fluid retrieval container such that said first end of said tube is located in a first position above a ground plane, and said second end of said tube is located in a second position closer to said ground plane than said first position; and a holder disposed on said support member, said holder retaining said middle portion of said tube between said first position and said second position and readily releasing said middle portion of said tube when a predetermined pulling force less than a force required to forcibly remove said catheter from said human being is applied to said tube, wherein said holder includes a pouch comprising a first portion of material having a shape with at least two sides and a second portion of material having a shape corresponding to the shape of said first portion of material, said first portion of material being joined to said second portion of material along a pair of corresponding sides, a second pair of corresponding sides of said first and second portions of material remaining unjoined to form a pouch opening, wherein each of said first portion of material and said second portion of material is provided with a stiffener to stiffen said pouch opening.

2. A device as recited in claim 1, wherein said first portion includes a first pocket and a first stiffener supported in said first pocket, and wherein said second portion includes a second pocket and a second stiffener supported in said second pocket.

* * * * *